United States Patent
Frid

(10) Patent No.: US 8,715,338 B2
(45) Date of Patent: May 6, 2014

(54) LUMINAL ENDOPROSTHESIS FOR THE OCCLUSION OF AN ANEURYSM AND METHOD OF MANUFACTURING SUCH AN ENDOPROSTHESIS

(76) Inventor: Noureddine Frid, Beersel (BE)

(*) Notice: Subject to any disclaimer, the term of this patent is extended or adjusted under 35 U.S.C. 154(b) by 1276 days.

(21) Appl. No.: 11/628,383

(22) PCT Filed: May 30, 2005

(86) PCT No.: PCT/EP2005/052448
§ 371 (c)(1),
(2), (4) Date: Nov. 1, 2007

(87) PCT Pub. No.: WO2005/117718
PCT Pub. Date: Dec. 15, 2005

(65) Prior Publication Data
US 2011/0046719 A1   Feb. 24, 2011

(30) Foreign Application Priority Data
Jun. 3, 2004  (BE) .................................. 2004/0277

(51) Int. Cl.
*A61M 29/00* (2006.01)
*A61F 2/86* (2013.01)

(52) U.S. Cl.
USPC ........................................... 623/1.3; 606/200

(58) Field of Classification Search
USPC ............................ 623/1.3, 1.31; 606/194, 200
See application file for complete search history.

(56) References Cited

U.S. PATENT DOCUMENTS

| | | | | |
|---|---|---|---|---|
| 5,697,969 A | * | 12/1997 | Schmitt et al. | 623/1.44 |
| 5,846,261 A | * | 12/1998 | Kotula et al. | 606/213 |
| 6,254,571 B1 | * | 7/2001 | Hart | 604/107 |
| 6,267,775 B1 | * | 7/2001 | Clerc et al. | 606/198 |
| 6,395,021 B1 | * | 5/2002 | Hart et al. | 623/1.15 |
| 7,105,021 B2 | * | 9/2006 | Edens et al. | 623/1.5 |
| 2001/0000797 A1 | | 5/2001 | Mazzocchi | |
| 2002/0161392 A1 | * | 10/2002 | Dubrul | 606/200 |
| 2003/0195553 A1 | * | 10/2003 | Wallace et al. | 606/200 |
| 2004/0039435 A1 | | 2/2004 | Hancock et al. | |
| 2005/0107823 A1 | * | 5/2005 | Leone et al. | 606/200 |
| 2005/0228434 A1 | * | 10/2005 | Amplatz et al. | 606/200 |

FOREIGN PATENT DOCUMENTS

WO   WO 02/00139 A1   1/2002
WO   WO 0247579 A1 *  6/2002

OTHER PUBLICATIONS http://dictionary.reference.com/browse/integrated?s=t&path=/ printed Sep. 13, 2013.*

* cited by examiner

*Primary Examiner* — Thomas J Sweet
*Assistant Examiner* — Cheryl Miller
(74) *Attorney, Agent, or Firm* — Christie, Parker & Hale, LLP

(57) ABSTRACT

A luminal endoprosthesis for treating aneurysms, particularly aneurysms located at an arterial bifurcation. One feature of the endoprosthesis is a tubular armature that can expand radially from a compressed state to an expanded state. A further feature of the endoprosthesis, when in the expanded state, is a lenticular head whom axis coincides with that of the tubular armature, and which can be inserted into an aneurysm pocket. A method of manufacturing such an endoprosthesis is also described.

4 Claims, 3 Drawing Sheets

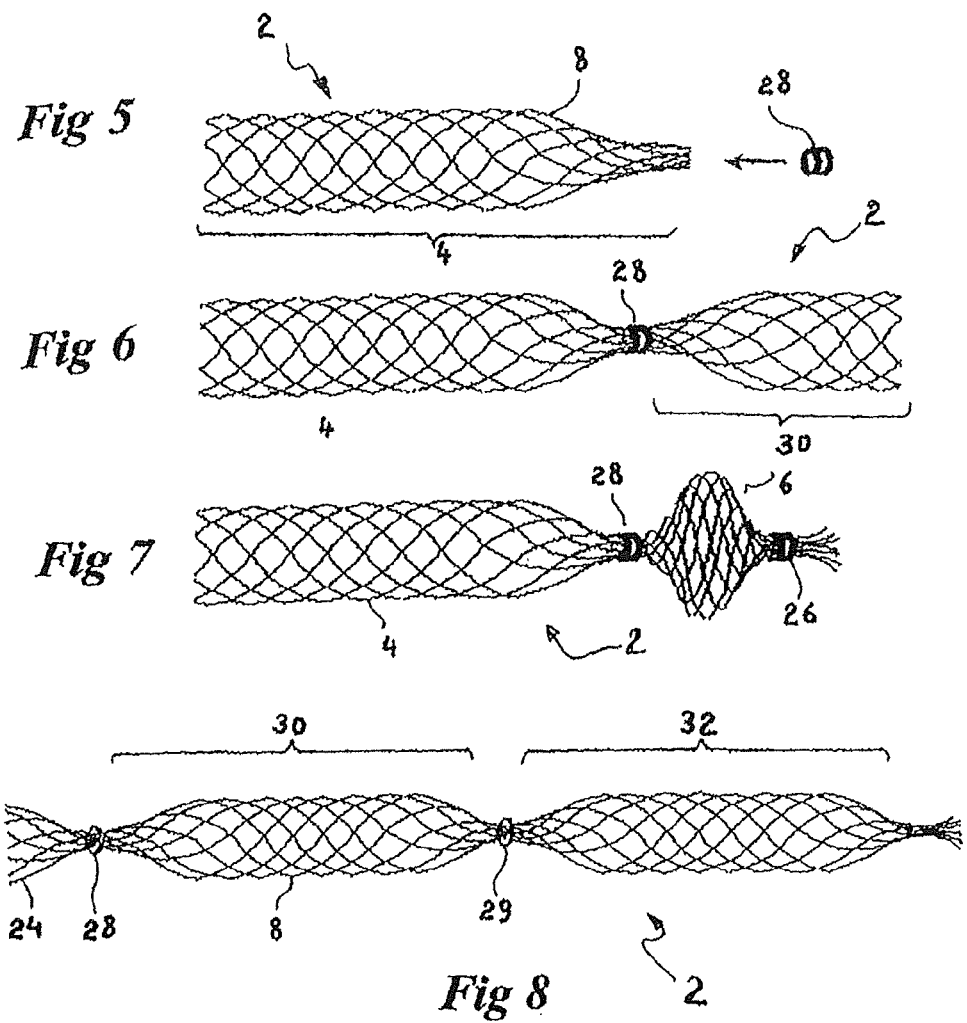

LUMINAL ENDOPROSTHESIS FOR THE OCCLUSION OF AN ANEURYSM AND METHOD OF MANUFACTURING SUCH AN ENDOPROSTHESIS

FIELD OF THE INVENTION

The invention relates to a luminal endoprosthesis comprising a tubular armature extending along an axis, radially expansible from a contracted state to an expanded state and intended for treating aneurysms.

The invention also relates to a method of manufacturing such an endoprosthesis.

STATE OF THE ART

An arterial aneurysm is a particularly feared affliction that has to be treated quickly, especially by surgery. This is because the rupture of an aneurysm may lead to serious irreversible lesions, especially when it occurs in the cerebral region.

Aneurysms are pockets that form in the path of an artery, at a weaker region in the arterial wall, under the effect of haemodynamic variations. Aneurysms, as they grow, show a progressive increase in volume (with an accompanying thinning of their wall) and, when they have reached maturity, present the form of a pocket of variable size connected to the arterial wall via a neck.

To limit the growth of aneurysms and thus prevent them possibly rupturing, there are intervention techniques in existence which rely especially on occluding the aneurysm pocket of the arterial lumen.

A first method is to cause the blood contained in the pocket to coagulate by introducing biocompatible, particularly metal, filaments into it.

However, this technique, which requires delicate manipulations, has disadvantages. Specifically, it is limited by the shape of the aneurysm pocket and by the width of the neck. Furthermore, phenomena of local ischemia have been observed, due to the erratic migration of the filaments under the action of the blood flow, and also aneurysm ruptures caused directly by the filaments pressing against the aneurysm wall.

Application EP 1 316 293 also discloses a device for treating aneurysms which comprises a circular support membrane, resting on spokes, and to which an occlusion piece made of an expanding material (polymer, biocompatible foam) is fixed. The device is introduced into the artery that is to be treated using a catheter and is released at the aneurysm. Once in place, the circular membrane rests on the neck of the aneurysm to block off its entry, while the occlusion piece deploys inside the aneurysm pocket. One disadvantage of polymers is that they degrade and the effect of solvents, which may be harmful.

A second method is to deposit a tubular endoprosthesis at the aneurysm so as to block off its neck. U.S. Pat. No. 4,878,906 discloses an endoprosthesis made of plastic, having the shape of a flexible sleeve, which is introduced into the artery that is to be treated using a catheter and is then released at the aneurysm.

Document FR 2 797 176 describes another endoprosthesis, also intended for occluding aneurysms. It consists of a curved plate which, once in place, hugs the internal wall of the vessel. It is formed of a central element which blocks off the aneurysm, and of retaining elements that can rest against the internal wall of the vessel in order to immobilize it.

However, these technologies reach their limitations in the case of the treatment of aneurysms formed at the bifurcation of an artery, as is particularly the case of intracerebral aneurysms, which are the most common. These actually make up almost ¾ of recorded cases.

The problem is that when using filaments or occlusion pieces, these would have a tendency to migrate under the action of the blood flow, the hydrodynamics of which are turbulent in the vicinity of the bifurcation.

As far as tubular endoprostheses are concerned, these would not prove satisfactory because, given their geometry, they are able to cover just one branch of the bifurcation, which leads to practically no reducing or preventive effect against a possible rupture of the aneurysm wall, given that this wall is still subjected to the pressure wave of the blood flow.

SUMMARY OF THE INVENTION

One object of the invention is to provide a luminal endoprosthesis which is suited to occluding an aneurysm located at an arterial bifurcation, and which is also easy to position.

Another object of the invention is to provide an endoprosthesis which is also simple to manufacture.

The subject of the invention is an endoprosthesis which comprises, in the expanded state, at least one lenticular head, the axis of which coincides with that of the endoprosthesis, and can be inserted in an aneurysm pocket. This at least one lenticular head is arranged at one end of a tubular armature.

Studies have shown that by modifying the haemodynamics at the aneurysm pocket, particularly by lowering the blood pressure, it was possible to encourage it to thrombosis and therefore be reabsorbed. Thus, by virtue of the head or heads of lenticular shape of the invention, which are placed within the inert cavity of the aneurysm pocket, the blood flow within the said pocket is disrupted in order to reduce its speed.

The tubular shape of the armature also allows the endoprosthesis to anchor effectively at an arterial bifurcation because the tubular part is placed in such a way that it extends into the main artery and rests against the walls thereof.

Advantageously, the armature of the endoprosthesis is a meshed structure, which can be obtained in particular by braiding filaments. The braiding may be either monolayer or multilayer.

This second form of braiding is advantageous both from the point of view of its elasticity and from the point of view of its flexibility. Specifically, unlike the other arteries, the cerebral arteries are sinuous (problem of access) and fragile (can easily tear) particularly, as goes without saying, in the region of an aneurysm. Furthermore, it has better integrity over time. What is more, it plays a part in effectively attenuating the pressure waves generated by the blood flow.

Because of the presence of the lenticular head or heads of meshed structure, depending on the size of the aneurysm, the particles (clots) that form during the thrombosis and which may detach from the arterial wall are trapped by the meshed structure of the said lenticular head or heads. This then prevents the risk of clots migrating to other arteries.

The latticework armature may also be produced by laser cutting a hollow tube.

The armature is made of an elastic biocompatible alloy.

Advantageously, this alloy has shape memory. This is because by using an alloy of appropriate composition and carrying out an appropriate heat treatment, it is possible to manufacture a self-expanding endoprosthesis, the deployment of which is facilitated by a phase transition caused by the internal temperature of an organism into which the said endoprosthesis is inserted.

Thus, below its transition temperature the endoprosthesis is very easy to handle, which means that it can easily be brought to size, brought to its smaller diameter and introduced into an applicator without experiencing damage.

As a preference, the biocompatible alloy is chosen from nickel/titanium alloys (NITINOL®) or nickel/chrome/cobalt based alloys (ELGILOY®) or PHYNOX®).

The endmost lenticular head is preferably crimped.

Another subject of the invention is a method of manufacturing such an endoprosthesis, which comprises the following operations:

forming a substantially tubular meshed armature from a biocompatible alloy;
shaping the said armature by mechanical stressing in order to form the at least one lenticular head;
subjecting the said armature to a heat treatment to stabilize the structure;
sealing the open distal end of the endmost lenticular head.

The armature is shaped by slipping a diameter limiting device (for example an annulus) over the said armature followed by compression of a free end of the armature towards the diameter limiter. After the heat treatment, the diameter limiter is then removed from the tubular armature.

Thus, the manufacture of the endoprosthesis according to the invention calls upon a small number of operations, and this has a favourable impact on production costs.

BRIEF DESCRIPTION OF THE DRAWINGS

These aspects, together with other aspects of the invention, will be clarified in the detailed description of particular embodiments of the invention, reference being made to the drawings, in which:

FIGS. 5, 6, 7 are schematic views, with breaks, of the operations of manufacturing the endoprosthesis according to the invention;

FIG. 8 is a schematic view of a step in the method of manufacture of the endoprosthesis, in which step two sausages are formed using two annuluses.

The figures are not drawn to scale. In general, similar elements are denoted by similar references in the figures.

DETAILED DESCRIPTION OF PARTICULAR EMBODIMENTS

Figure 1:
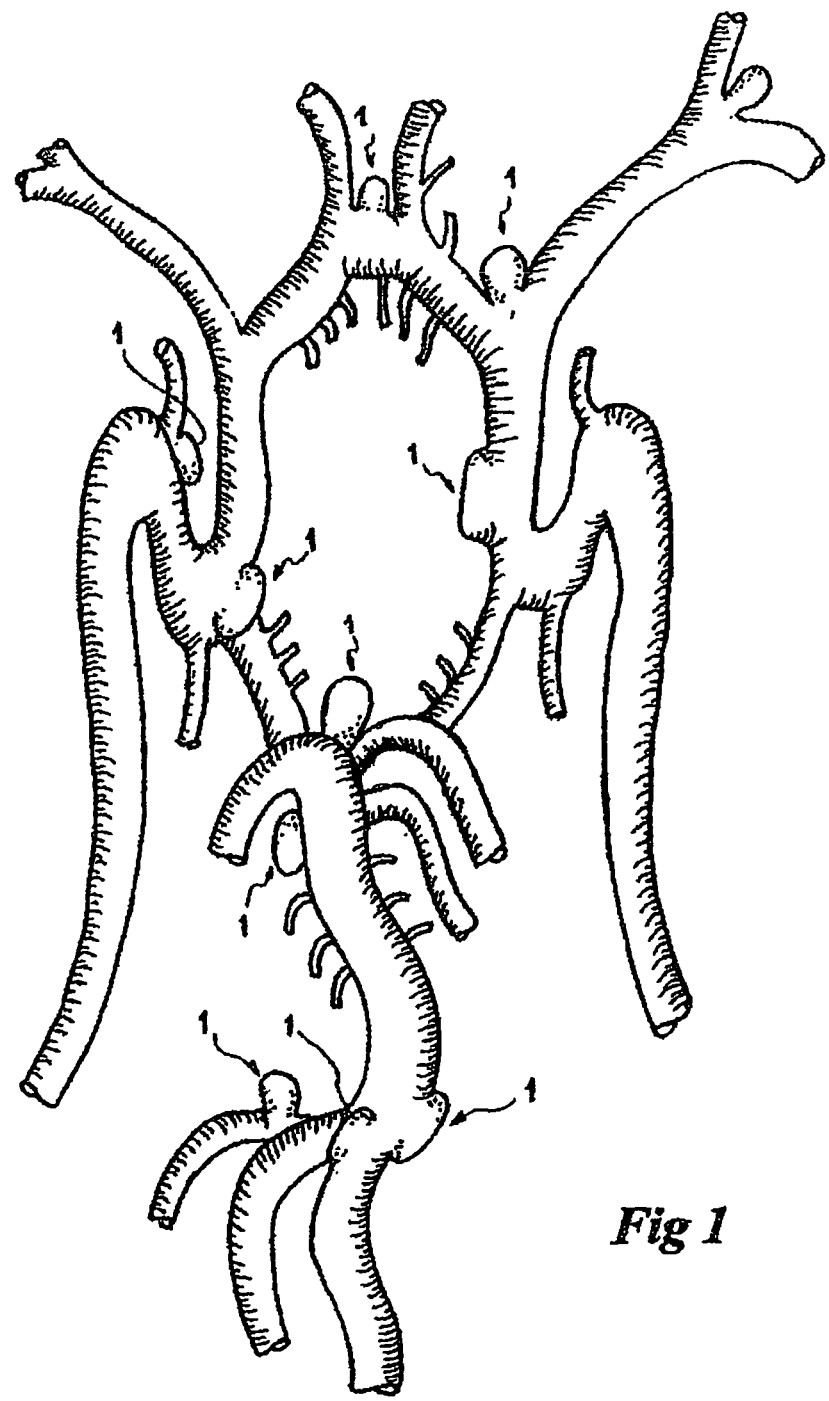
FIG. 1 is a schematic view of the locations of intracerebral aneurysms in humans.

FIG. 1 demonstrates the benefit of having a tool able to act on intracerebral aneurysms 1 which, should they rupture, could lead to the paralysis or death of the patient. As can be seen clearly, most of these aneurysms 1 are situated in regions of arterial bifurcation, particularly in the circle of Willis or its main branches.

The treatment of such aneurysms using the known tools of the prior art is not satisfactory because either they are not suitable for placement at the bifurcation or their effectiveness is modest and remains limited over time.

Figure 2:
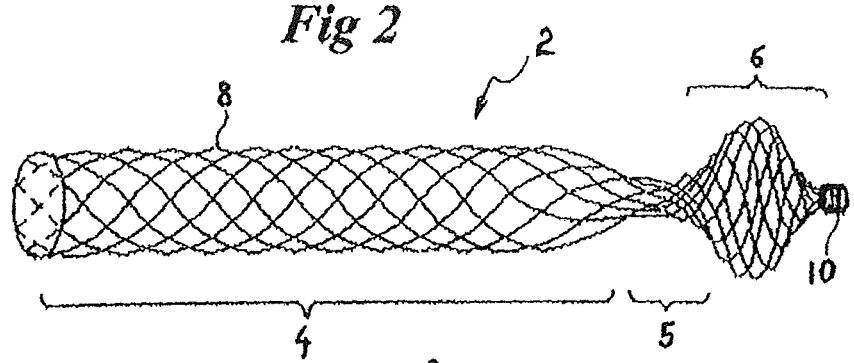
FIG. 2 is a schematic perspective view of a first embodiment of the endoprosthesis according to the invention, in the deployed state.

FIG. 2 is a schematic depiction in elevation, in the deployed state, of a first embodiment of an endoprosthesis 2.

The endoprosthesis 2 comprises a tubular armature 4 a first end of which terminates, via a throat 5, in a head of lenticular shape 6. The armature of the endoprosthesis 2 is a meshed structure, here obtained by braiding filaments 8. The material of the filaments is an elastic alloy and is advantageously chosen from shape memory alloys, such as nickel/titanium based alloys for example.

In order to give the endoprosthesis 2 good mechanical strength and good integrity over time, the braiding used is a multilayer braiding, as described in application WO 02/47579. However, conventional monolayer braiding may also be suitable.

The free end of the lenticular head 6 comprises a means of crimping the filaments 8 which, in this instance, is a ring 10. This ring 10 is rounded so as to form a non-traumatic head. As an option, in order to allow the endoprosthesis to be located after it has been introduced into the organism, the ring 10 is covered with or made of a radio-opaque material.

It is possible, also, to replace the crimping by a retracting of the end filaments 8 inside, the head 6 in this case then adopting the shape of an onion.

Figure 3:
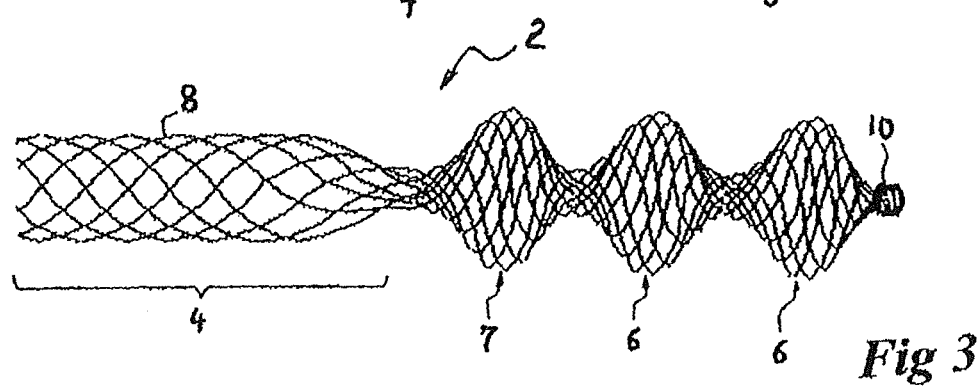
FIG. 3 is a schematic perspective view of a second embodiment of the endoprosthesis according to the invention.

FIG. 3 is an elevation of another embodiment of the endoprosthesis 2, in which the free end of the tubular body 4 comprises 3 lenticular heads 6, 6, 7.

This embodiment is particularly suitable for treating large sized aneurysm pockets ("giant" aneurysms, to adopt the current terminology). This is because the presence of several heads 6, 7 in the aneurysm cavity is even better at disrupting the blood flow and encourages thrombosis. Furthermore, the multiplicity of the heads 6, 7 tends to give the endoprosthesis 2 better stability.

Figure 4:
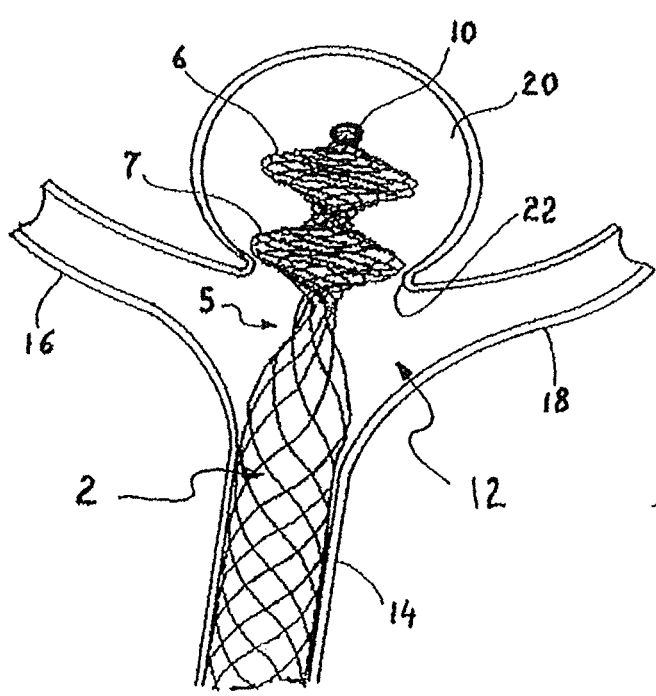
FIG. 4 is a schematic view of an aneurysm, situated at an arterial bifurcation, in which an endoprosthesis according to the invention is deployed.

FIG. 4 is a schematic depiction of an arterial bifurcation 12 afflicted by an aneurysm and treated by an endoprosthesis 2 according to the invention.

The arterial bifurcation 12 comprises a main artery 14, which divides into a first branch 16 and a second branch 18. The aneurysm pocket 20 is located at the intersection of the main artery 14 with the two branches 16, 18 and is connected to the arterial wall by a neck 22.

Aneurysms are often located at this location because the arterial wall is weakest there, given that it is subjected to strong haemodynamic variations. Furthermore, as soon as the pocket 20 has begun to form, the turbulence (vortices) that develop therein rapidly increase its size.

The aneurysm pocket 20 of FIG. 4 is treated using an endoprosthesis 2 according to the invention.

The endoprosthesis 2 has been introduced by means of a catheter of appropriate shape and then released. Under the effect of the temperature of the organism (in the case of shape memory alloys) and because of their inherent elasticity (in the case of conventional alloys such as PHYNOX®), the two lenticular heads 6, 7 deploy in the aneurysm pocket 20, while the tubular body 4 rests along the wall of the main artery 14 via which the endoprosthesis 2 was introduced.

It will be noted that the nominal diameter of the tubular part 4 corresponds substantially to that of the main artery 14 so as to hold in place firmly.

The dimensions of the endoprosthesis are quite obviously selected to suit the size of the aneurysm that is to be treated.

It will be noted that the lenticular heads 6, 7, once deployed, are dimensioned in such a way as not to press against the arterial wall of the aneurysm 20. Only the convex side of the proximal lenticular head 7 rests on the neck 22, a place where the arterial wall is still relatively intact because it is not greatly distended. Furthermore, the practitioner will make sure that the endmost lenticular head 6 does not press against the capped closed end of the pocket, in order to avoid the risk of puncturing it.

Because of the presence of the lenticular heads 6, 7 in the aneurysm pocket 20, the blood flow flowing within this pocket is greatly slowed and disrupted. The blood, being subjected to far less turbulent haemodynamics, can coagulate in the normal way, thus giving rise to natural thrombosis of the aneurysm.

The meshed structure of the endoprosthesis is advantageous because, aside from its thrombosis-inducing effect, it causes the lenticular heads 6, 7 to act as screens which hold back the clots that form and that could detach from the aneurysm pocket 20 during the thrombosis process.

The throat 5 of the endoprosthesis 2, lying between the proximal head 7 and the tubular body 4 does not disrupt the distribution of the blood flow between the two branches 16, 18 of the bifurcation. It moreover acts as a secondary filter, able to intercept any large clots that may have become detached upstream, thus avoiding occlusions in the capillaries situated downstream.

FIG. 5 is a schematic depiction of a first operation in the method of manufacturing an endoprosthesis according to the invention. The endoprosthesis 2, before being shaped, is in the form of a tubular armature 24 comprising braided filaments 8. A first free end terminates in the filaments that make up the armature 24.

The shaping step depicted in FIG. 6 begins by slipping an annulus 28, which acts as a diameter limiter, onto the tubular body 4. It is conceivable for the role of diameter limiter to be played by an annulus 28, as described here, or by any other appropriate device.

The positioning of the annulus 28 along the tubular body 4 determines the size that is to be given to the lenticular head 6.

This is because, during the next step (FIG. 7), the sausage-shaped tubular portion 30 running between the annulus 28 and the free end, is compressed axially towards the annulus 28. The compression movement causes the sausage 30 to inflate and it deforms to adopt a substantially lenticular shape 6.

The amount of deformation is dependent on the positioning of the annulus 28 relative to the distal free end. Thus, the closer the annulus 28 is to the said distal end, the more limited the deformation will be and therefore the less the lenticular head 6 will grow. By contrast, the further the annulus 28 is from the distal free end, the larger the lenticular head 6 will be.

Once the appropriate shape has been achieved, in the case where the filaments 8 are made of shape memory alloy, the endoprosthesis undergoes a heat treatment that causes it to undergo a phase transition so as to make it memorize its expanded shape.

In the case where the material used is a nickel/chrome/cobalt based alloy, the endoprosthesis undergoes a high-temperature heat treatment to fix and stabilize the structure and eliminate the stresses in its metallographic structure.

Following this treatment, the endoprosthesis 2 is cooled and the annulus 28 is then disengaged from the endoprosthesis 2.

The filaments 8 of the free end are then gathered together to be crimped by means, for example, of a non-traumatic radio-opaque ring 26.

The endoprosthesis 2 is either braided or trimmed to size or made to the right size by cutting.

To treat large aneurysms the diameter of which may reach 15 to 25 mm or even more, it is advantageous to have endoprostheses 2 comprising several lenticular heads. The method of manufacture of such an endoprosthesis is based on the method described above.

Thus, to manufacture an endoprosthesis including two lenticular heads 6, 7, use will be made of a second annulus 29 slipped around the tubular armature 24 in such a way as to form two sausage-shaped sections 30, 32 as depicted in FIG. 8. The sausages 30, 32 are then compressed axially so as to each to form a lenticular head 6, 7.

As described above, if use is made of a shape memory metal, the endoprosthesis 2 then undergoes a suitable heat treatment to cause it to memorize its expanded shape.

The person skilled in the art will understand that the lenticular heads may be the same size or different sizes, according to the relative positionings of the annuluses 28, 29 one with respect to the other, thus making it possible to treat aneurysms of different configurations.

The examples given above refer to meshed armatures made up of filaments 8, but it is obvious to the person skilled in the art that the endoprosthesis 2 according to the invention may be produced by different braiding methods and also designed on the basis of a hollow tube, the meshed structure of which may be obtained, for example, by laser cutting.

The method of placement of the endoprosthesis according to the invention, in an aneurysm located at an arterial bifurcation, is summarized below.

The practitioner places the endoprosthesis, while at the same time compressing it, inside an insertion tool suited to the size of the artery via which it will be introduced.

The endoprosthesis is brought to the site that is to be treated and is then released. Because of the inherent elasticity of the structure, the armature expands in such a way that the at least one lenticular head deploys on entering the aneurysm, at the neck, far from the aneurysm wall, while the stabilizing tubular part of the endoprosthesis extends along the main artery on the opposite side to the aneurysm.

It will be obvious to the person skilled in the art that the present invention is not restricted to that which has been disclosed and described in particular hereinabove. The invention lies in the exhibiting of all novel characteristics and in each combination of these characteristics. The numerical references in the claims do not restrict the scope of their protection. The use of the verbs "comprise, contain or include" and their conjugated forms does not exclude the presence of elements other than those listed in the claims. The use of the indefinite article "a/an/one" before an element does not exclude the presence of a plurality of such elements.

The present invention has been described in terms of specific embodiments which are one illustration of the invention and must not be considered as being limiting.

The invention claimed is:

1. A permanent luminal endoprosthesis adapted for insertion into a vessel adjacent an aneurysm, the aneurysm comprising an aneurysm pocket and an aneurysm wall, the permanent luminal endoprosthesis being radially expandable from a contracted state to an expanded state and comprising a tubular armature extending along an axis; at least one lenticular head having an axis that coincides with the axis of the tubular armature; and a throat connecting the at least one lenticular head to the tubular armature, wherein each of the tubular armature, the throat, and the at least one lenticular head comprise a multilayer braid that together form a single integrated structure, wherein in the expanded state, the tubular armature defines a first diameter and the throat defines a truncated cone shape connected at a proximate end to a distal end of the tubular armature and narrowing at a distal end to a second diameter, the second diameter being smaller than the first diameter with the at least one lenticular head connected to the distal end of the throat, the tubular armature being capable of being expanded up to a diameter of the vessel at the aneurysm, the at least one lenticular head having such dimensions and shape that when inserted into the aneurysm pocket, only a proximal side of a proximal lenticular head of the at least one lenticular head rests on a neck of the aneurysm with none of the at least one lenticular head(s) pressing against a wall of the aneurysm, so as to avoid risk of puncturing the wall, and wherein, an endmost lenticular head of the at least one lenticular head(s) comprising a free end which is retracted into said endmost lenticular head.

2. The luminal endoprosthesis according to claim 1, wherein the endmost lenticular head of the at least one lenticular head(s) is crimped.

3. The luminal endoprosthesis according to claim 1, wherein the tubular armature is made of a biocompatible metal alloy.

4. The luminal endoprosthesis according to claim 3, wherein the biocompatible metal alloy is chosen from nickel/titanium or cobalt/chrome/nickel alloys.

\* \* \* \* \*